United States Patent
Sass

(10) Patent No.: US 7,235,590 B2
(45) Date of Patent: Jun. 26, 2007

(54) USE OF TREOSULFAN AND DERIVATIVES THEREOF FOR TREATING MULTIPLE SCLEROSIS

(75) Inventor: Gretel Sass, Hamburg (DE)

(73) Assignee: Medac Gesellschaft fur Klinische Spezialpraparate mbH, Hamburg (DE)

( * ) Notice: Subject to any disclaimer, the term of this patent is extended or adjusted under 35 U.S.C. 154(b) by 5 days.

(21) Appl. No.: 10/524,144

(22) PCT Filed: Aug. 12, 2003

(86) PCT No.: PCT/EP03/08957

§ 371 (c)(1),
(2), (4) Date: Jul. 26, 2005

(87) PCT Pub. No.: WO2004/016263

PCT Pub. Date: Feb. 26, 2004

(65) Prior Publication Data

US 2006/0041015 A1    Feb. 23, 2006

(30) Foreign Application Priority Data

Aug. 13, 2002 (DE) ............................... 102 37 146

(51) Int. Cl.
 *A61K 31/10* (2006.01)
 *A61K 33/04* (2006.01)
 *A01N 41/10* (2006.01)
 *A01N 59/02* (2006.01)

(52) U.S. Cl. ...................... 514/903; 424/703; 514/708; 514/709; 514/711

(58) Field of Classification Search ................ 424/703; 514/708, 709, 711, 903
See application file for complete search history.

(56) References Cited

FOREIGN PATENT DOCUMENTS

WO         01 32154 A      5/2001
WO         WO 01/32154     5/2001

OTHER PUBLICATIONS

Fridman, Igor Surface area of Human Skin 2001.*
H. Openshaw et al., "Peripheral blood stem cell transplantation in multiple sclerosis with busulfan and cyclophosphamide conditioning: Report of toxicity and immunological monitoring", Biology of Blood and Marrow Transplantation, vol. 6, No. 5a, pp. 563-575, XP002263510.
Rieckmann, Immunmodulatorische Therapie der Multiplen Sklerose, 2002: 109-118.
Goodin et al, Neurology 58, Jan. 2002, pp. 169-178.
Specialist information "Novantron®" (Wyeth Pharma GmbH), Jan. 2002.
Weissert et al, J. Clin. Invest., 1998, 102:1265-1273.
Weissert et al, The Journal of Immunology, 1998, 160:681-690.
Weissert et al, The Journal of Immunology, 2001, 166:7588-7599.
Hauser et al, N. Engl. J. Med., 1983, 308:173-180.
Openshaw et al, Biology of Blood and Marrow Transplantation 2000, 6:563-575.

* cited by examiner

*Primary Examiner*—Johann Richter
*Assistant Examiner*—Ernst V Arnold
(74) *Attorney, Agent, or Firm*—Nixon & Vanderhye P.C.

(57) ABSTRACT

The invention relates to the use of treosulfan and/or derivatives thereof for producing a pharmaceutical composition used in the treatment of multiple sclerosis.

30 Claims, 18 Drawing Sheets

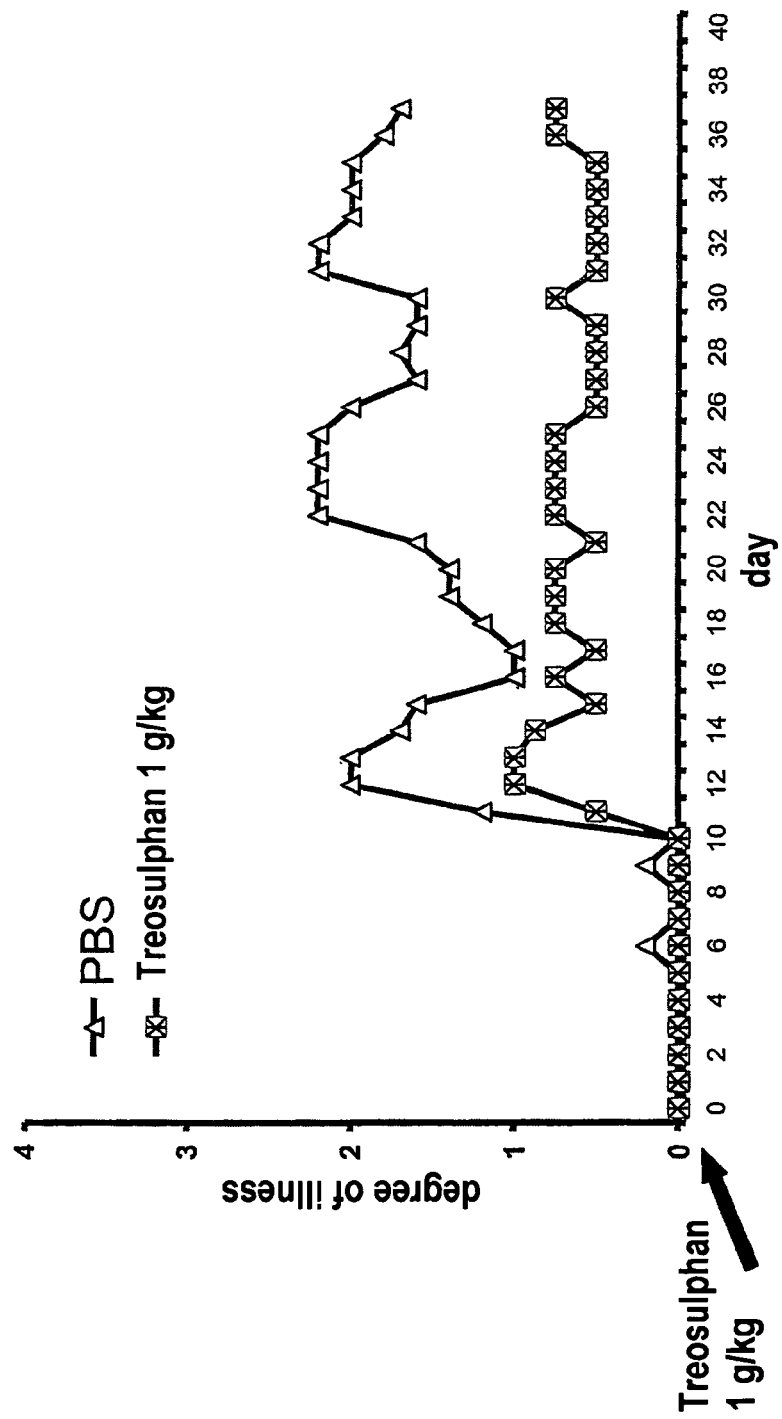

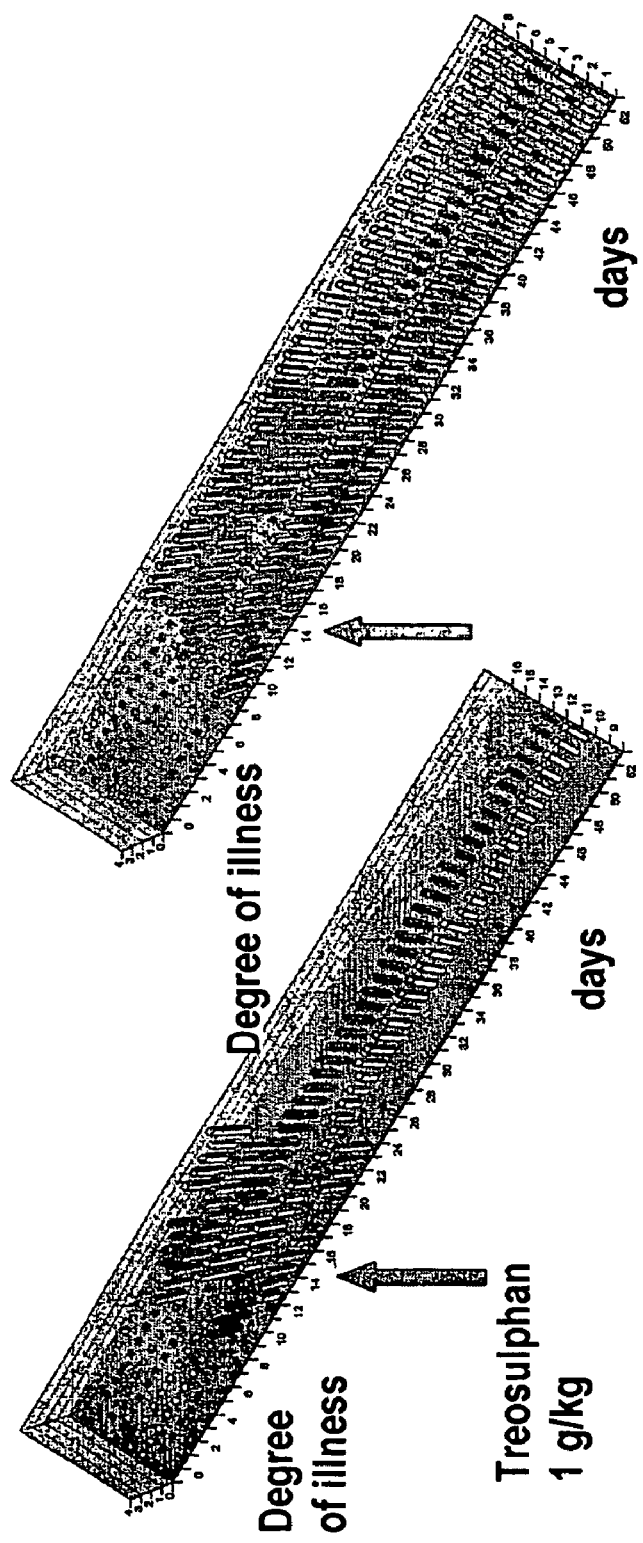

USE OF TREOSULFAN AND DERIVATIVES THEREOF FOR TREATING MULTIPLE SCLEROSIS

This application is a 371 of PCT/EP03/08957 filed on Aug. 12, 2003.

The present invention relates to the use of treosulfan and derivatives thereof for treating Multiple sclerosis.

Multiple sclerosis (MS) is a neurological disease which affects more than a million people worldwide. MS is an inflammatory state which destroys the myelin of the central nervous system (CNS) and causes neurological impairments as well as frequently also serious disabilities. The etiology of MS has so far remained unknown, it being generally assumed that the disease is mediated by some kind of autoimmune process which is possibly triggered by an infection and superimposed by a genetic predisposition. Following a mostly insidious, rarely sub-acute or acute beginning in the 20$^{th}$ to 40$^{th}$ year of life, most frequently, a chronic-progressive or polycentric development with a tendency towards remission is observed. The different stages and forms of multiple sclerosis are subdivided into relapsing-remitting (RR) MS (at present approximately 80–85% of MS patients), primary progressive (PP) MS, with more than 50% of the patients with RR-MS finally developing a permanent deterioration with or without superimposed relapses (secondary progressive (SP) form of MS) over time. It is not clear whether the different disease progressions are based on the same or different pathophysiological processes.

For the treatment of the different phases and forms of MS, there are partially clear-cut treatment recommendations which are reflected in an immunomodulatory stepwise therapy of MS (P. Riekmann, "Immunmodulatorische Therapie der Multiplen Sklerose: Konsensusprotokolle im deutschsprachigen Raum und Nordamcrika" (immunomodulatory therapy of Multiple sclerosis: consensus protocols in the German-speaking region and North America) in "Multiple Sklerose: Kausalorientierte, symptomatische und rehabilitative Therapie" (Multiple sclerosis causally oriented, symptomatic and rehabilitative therapy) Springer Verlage Berlin—Heidelburg—New York 2002: 109–188). Corticosteroids have proved suitable for periodic therapy. For relapsing-remitting multiple sclerosis, immunologically effective substances reducing the number of relapses are available in the form of interferon β and glatriamer acetate. Interferon β is also effective in the case of secondary progressive MS insofar as relapses-remissions still occur at this stage.

For the therapy of the purely progressive MS, no drugs are available which have been clearly shown to be effective. Mitoxantrone and cyclophosphamide or methotrexate are used. According to the treatment guidelines of the MS Council for Clinical Practice Guidelines of 2002 (D. S. Goodin et at., Neurology 58 (2002) 169–178), the effectiveness of these substances is considered to be possible. Since cardiac side effects occur in the case of mitoxantrone with a cumulative dosage of 160 mg/m$^2$ and above (specialist information "Novantron®" (Wyeth Pharma GmbH), January 2002, Bundesverband der Pharmazeutischen Industrie c.V./FachInfo-Service, D-88322 Aulendorf), since damage to the lower urinary tract is possible in the case of cyclophosphamide and methotrexate frequently has gastrointestinal side effects, at least equally effective alternatives with fewer side effects are required.

In view of the still existing problems in the search for suitable active substances for the treatment of MS, it is consequently a task of the present invention to provide a pharmaceutical composition which is suitable for treating MS (including all development forms) and which does not exhibit the disadvantages known in the case of the active agents used so far.

The task is achieved according to the invention by the use of treosulfan or derivatives thereof.

Within the framework of the present invention it has surprisingly enough been found that treosulfan is not only extremely well tolerated but has also led to a clear improvement in the disease development in the case of MS patients.

Using the example of experimental autoimmune encephalomyelitis (EAE) which is recognized as animal model of human MS, the effectiveness of treosulfan was first of all examined. The effectiveness of the treosulfan treatment was investigated in comparison with an untreated control group and a group receiving mitoxantrone. In the first trials, treosulfan was applied on the day of immunisation, in another on day 14 following immunisation. Although it was not possible to reverse the damage that manifested itself by that day, a stabilisation could be observed in the case of the group treated with treosulfan, in contrast to the (untreated) control group in the case of which the disease progressed further. In the case of numerous test animals, however, a noticeable improvement occurred. Moreover, it was worth noting that in the treosulfan group, 7 out of 8 animals were still alive on day 53 whereas in the comparative group only 2 of 8 animals were still alive at that point. In the comparative group which received mitoxantrone, no greater effectiveness was observed than in the treosulfan group.

Treosulfan is (2S,3S)-threitol-1,4-bismethane sulphonate (L-threitol-1,4-bis(methane sulfonate); Chemical Abstracts Registry No. 299-75-2):

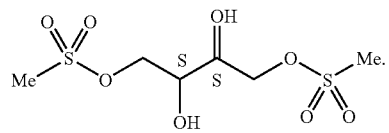

According to the invention, derivatives of treosulfan are also included such as e.g. busulfan (1,4-bis(methyl sulphonyloxy) butane), dimethyl busulfan (1,4-bis(methyl sulphonyloxy)-1,4-dimethyl butane; CA Registry No. 55-93-6), pentasulfan (1,5-dimesyl oxypentane; CA Registry No. 2374-22-3), hepsulfam (1,7-heptane diol disulphamate; CA Registry No. 96892-57-8) or similar substances which have led to similar results in initial control trials as treosulfan. To be considered for use are also treosulfan derivatives in which the methyl groups on the sulphur atom have been replaced (for example by (lower) alkyl substituents (linear or branched), in particular with 1 to 7 C atoms, e.g. ethyl, propyl, butyl, pentyl, hexyl and heptyl etc.) or substituted (replacement of one/several hydrogen atoms by one/several substituents such as e.g. isopropyl, tertiary butyl).

Busulfan has previously been used exclusively for conditioning patients before stem cell transplantation (compare Openshaw et al., Biology of Blood and Marrow Transplantation 2000, 6:563–575), with the aim of promoting the accretion of the transplant. In comparison, it has surprisingly enough been found in connection with the present invention that treosulfan and/or its derivatives, including busulfan are suitable directly for the treatment of MS. In comparison with the high risk and complicated approach of stem cell transplantation, the invention represents an independent and successful alternative.

The subject matter of the present invention is consequently the use of treosulfan and derivatives thereof for the preparation of a pharmaceutical composition for the treatment of MS. The above-mentioned substances, for example, are used as derivatives. According to the invention, combinations of treosulfan and/or a derivative thereof with one or several immunomodulatory substances, i.e. combination preparations containing—apart from treosulfan and/or a derivative thereof—one or several substances with an immunomodulatory effect such as e.g. interferon-β (IFN-β) and/or glatiramer acetate, as further active agent.

The pharmaceutical composition is preferably present in the form of a solution suitable for intravenous application (infusion); however, an oral formulation can also be considered for use.

The dosage is 1 to 10 g, preferably 3 to 9 g and particularly preferably 5 to 8 g treosulfan (and/or treosulfan derivative) per $m^2$ of body surface.

The pharmaceutical composition is used for the treatment of multiple sclerosis, including the treatment of relapsing-remitting, primary progressive and in particular secondary progressive MS.

The present invention will be explained in further detail by way of examples.

EXAMPLES

1. Preliminary Work

Firstly, several trials for the determination of the dosage of treosulfan were carried out in DA rats, a strain of rat particularly suitable for these trials (Dark Agouti strain) with myelin oligodendrocyte glycoprotein (MOG) induced experimental autoimmune encephalomyelitis (EAE). These rats represent an excellent model of multiple sclerosis (MS) since the clinical development and the lesion morphology (inflammation, demyelination, loss of axons and nerve cells) of MS can be reproduced.

It was found that a single dose of 1 g/kg bodyweight given by intraperitoneal administration was well-tolerated and capable of suppressing the disease (compare FIG. 1). The injected animals exhibited merely a substantial decrease in weight at the beginning of the treatment.

2. Investigation Of The Effect Of Treosulfan On MOG-EAE

2.1 Clinical characterisation

DA rats (10 animals per group) were treated either with a single dose of treosulfan (0.5 g/kg bodyweight) on the day of immunisation (p.i.) or with a three times repeated treosulfan application (0.5 g/kg bodyweight per application) at intervals of 1 day. PBS (phosphate buffered salt solution) was administered as control. In a further experiment, treosulfan (single dose: 0.5 g/kg bodyweight) was administered 2 weeks after immunisation. The total number of rats was 30 animals. The animals were observed clinically for the period of 40 days after initiation of the experiment and regularly examined neurologically.

2.2 Histopathological Examination Of The Lesions

On day 40, the rats were perfused and the central nervous system (CNS) was analysed histopathologically (for inflammation, demyclination and axion loss). (R. Weissert et al., J. Clin. Invest. 102 (1998), 1265–1273).

2.3 Immunological characterisation

In a second experiment, five rats each were characterised immunologically on day 12 and day 40 (total number of animals: n=30) following the immunisation with respect to T and B cell response (EliSpot (Autoimmun Diagnostika GmbH, D-72479 Strassberg) for IFN-secreting cells, proliferations, auto-antibody analysis). (R. Weissert et al., J. Immunol. 160 (1989), 681–690).

2.4 Haematological characterisation

To analyse the haematological status, blood was taken from the rats on day 0, day 5, day 14, and day 53 following immunisation and a determination of haemoglobin (Hb), reticulocytes, leukocytes, thrombocytes and crythrocytes carried out.

2.5 Results

To confirm preliminary data from dosage determination trials, the above-mentioned data were determined by using a meaningful number of animals.

The results are show in FIGS. 1–17. The results obtained confirm first of all the effectiveness of the treosulfan treatment in comparison with the untreated control group illustrated in FIGS. 1–3*a*. FIG. 4 shows the effectiveness of mitoxantrone under the same trial conditions. FIGS. 3 and/or 3*a* are different representations of the experiment in which treosulfan was administered on day 14 following immunisation. The damage which manifested itself by that day could naturally not be reversed. However, in contrast to the control group in the case of which the disease progressed further, a stabilisation was observed in the case of the group treated with treosulfan. In the case of some test animals, even a noticeable improvement took place.

Moreover, it was found that in the group treated with treosulfan, 7 out of 8 animals were still alive on day 53 whereas in the control group (untreated animals) only 2 out of 8 animals were still alive.

The tolerance of treosulfan is illustration in FIGS. 5–15. Changes to the blood picture are not documented.

It was, moreover, observed that the interleukin 12 (IL-12) and/or interferon-β (IFN-β) values were reduced in the treosulfan group (FIG. 16, 17). (R. Weissert et al., J. Immunol. 166 (2001), 7588–7599).

3. Execution Of Healing Trials On MS Patients

In the course of a first healing trial, 5 patients suffering from secondary progressive MS (SPMS patients) were treated. They consisted of 3 men aged 51/58/62 and two women aged 39/41.

As part of the therapy, treosulfan was administered in the form of a solution suitable for intravenous application (infusion). The patients were treated with a dosage of 5 $g/m^2$ body surface in each case at intervals of 4 weeks in the first quarter. Subsequently, a single treosulfan application (5 $g/m^2$ of treosulfan) took place per quarter.

In the case of two patients, an improvement of the ambulation index (S. L. Hauser et al. N. Engl. J. Med. 308 (1983) 173–178) was observed. No substance-related secondary effects were observed.

DESCRIPTION OF THE FIGURES

FIG. 2: Single i.p. treatment of MOG-EAE with treosulfan on the day of immunisation (repetition of the test).

FIG. 3: Single treatment of MOG-EAE with treosulfan on day 14 after immunisation.

Figure 1:
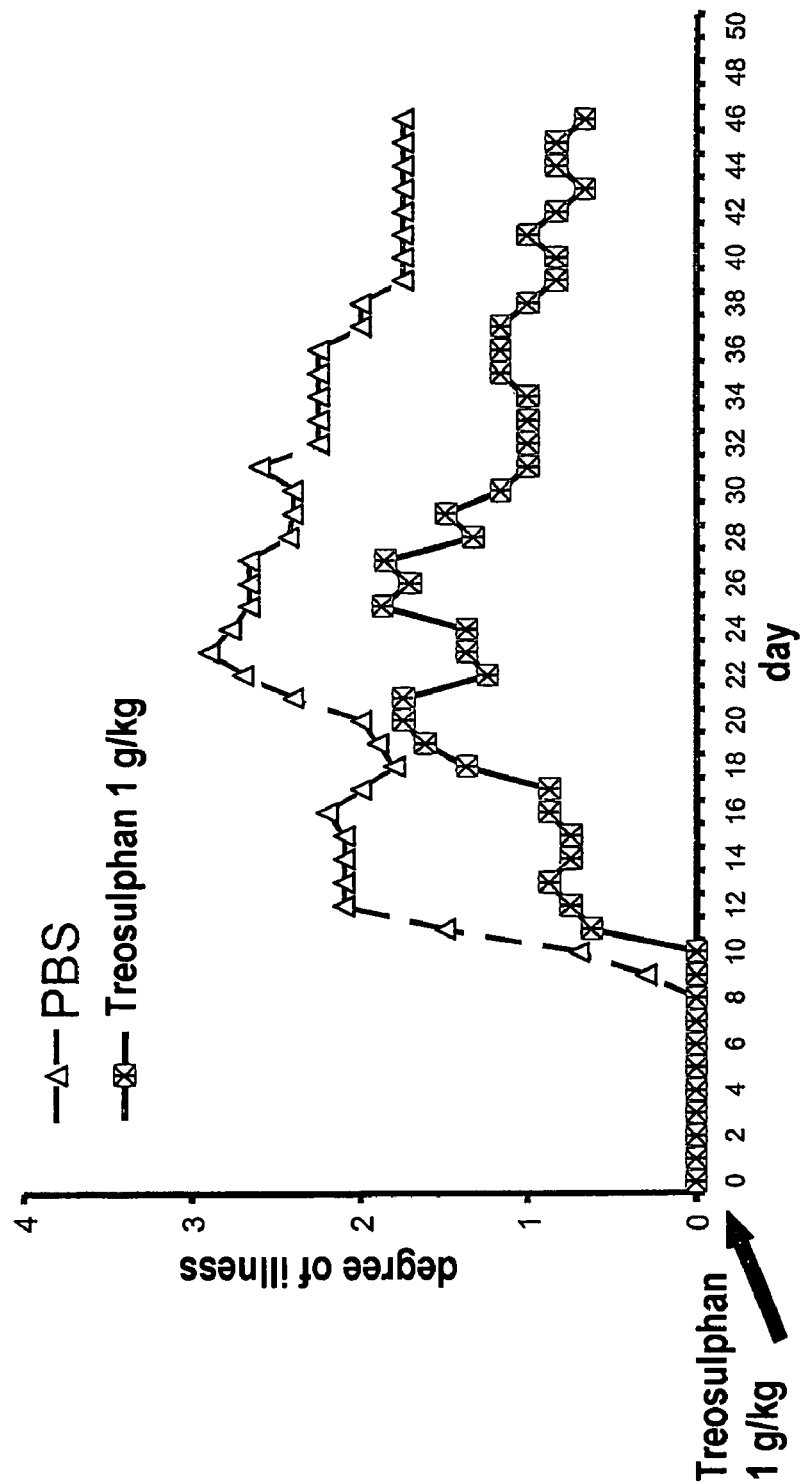
FIG. 1: Single i.p treatment of MOG-EAE with treosulfan on the day of immunisation.
Figure 3A:
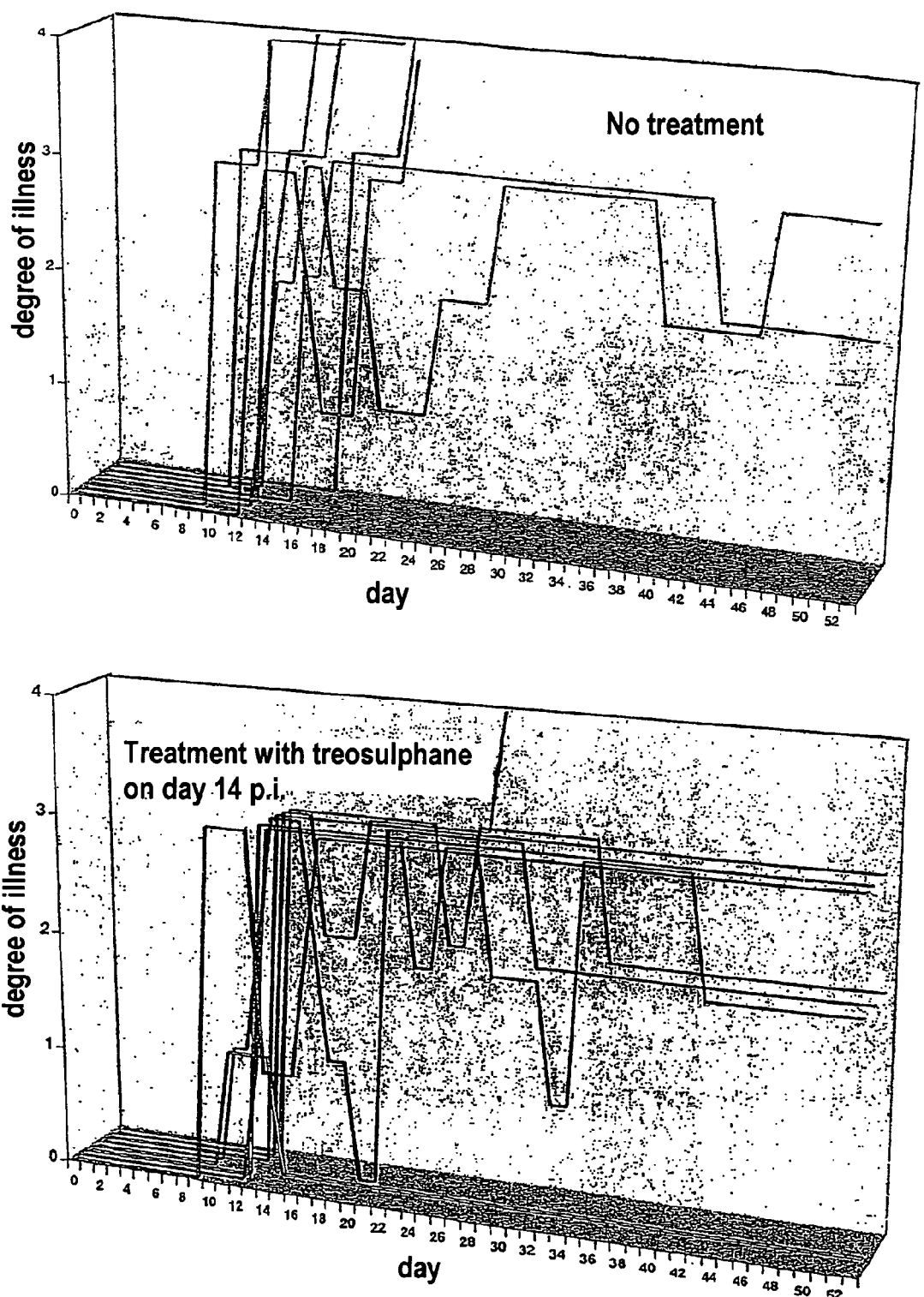
FIG. 3*a*: Single treatment of MOG-EAE with treosulfan on the day 14 after immunisation—different representation of the experiment.
Figure 4:
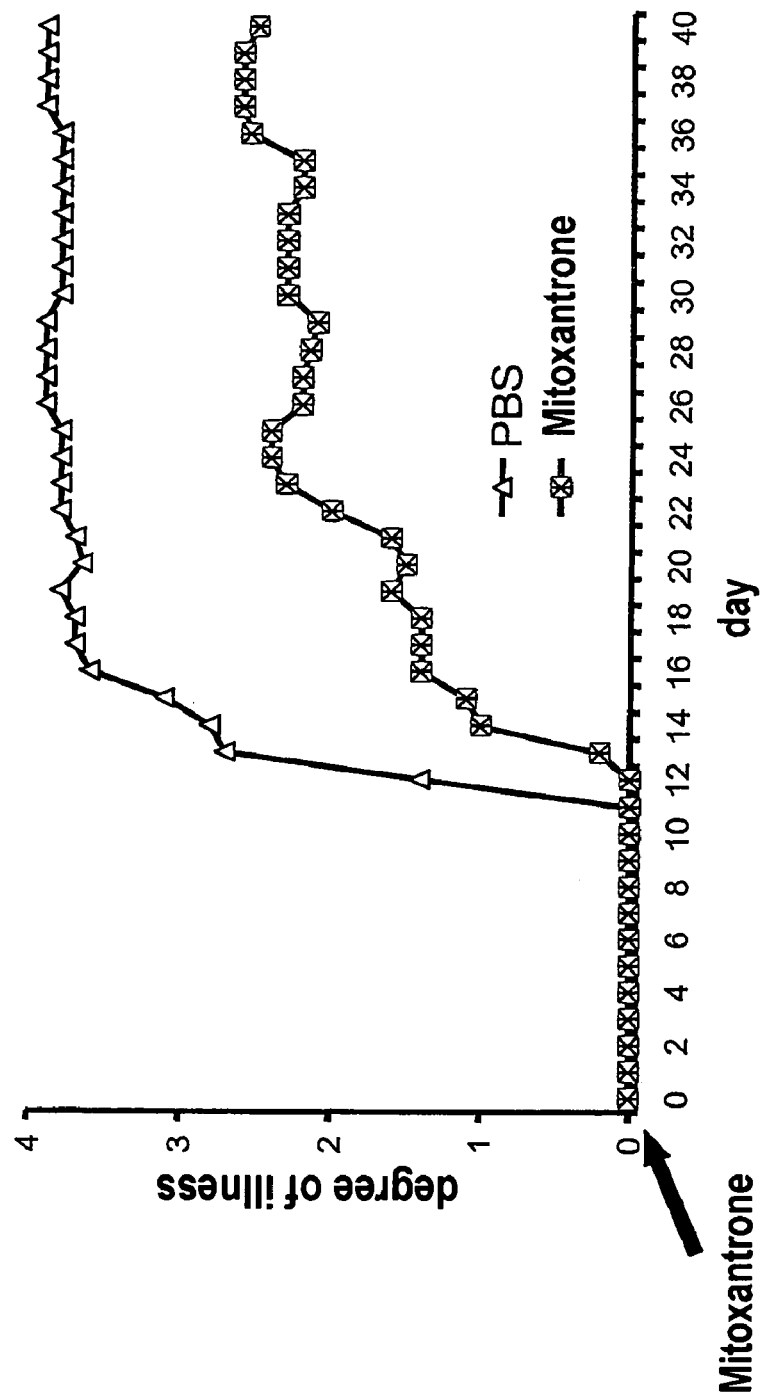
FIG. 4: Single i.p. treatment of MOG-EAE with mitoxantrone on the day of immunisation.
Figure 5:
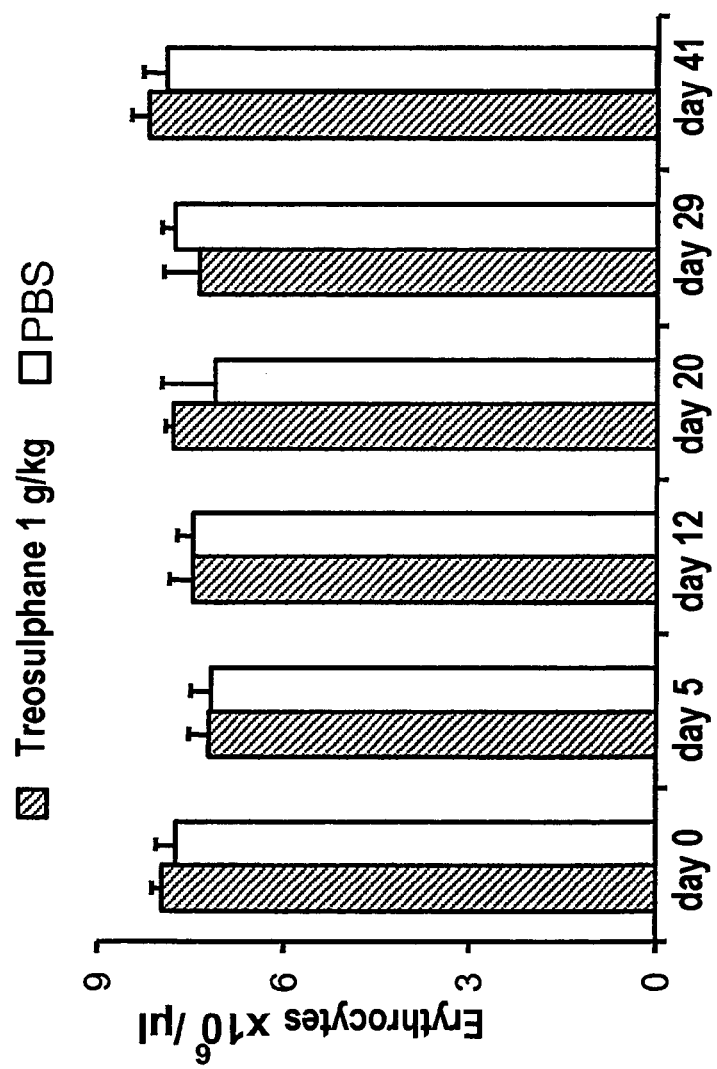
FIG. 5: Erythrocytes in MOG-EAE treatment with treosulfan on day 0.
Figure 6:
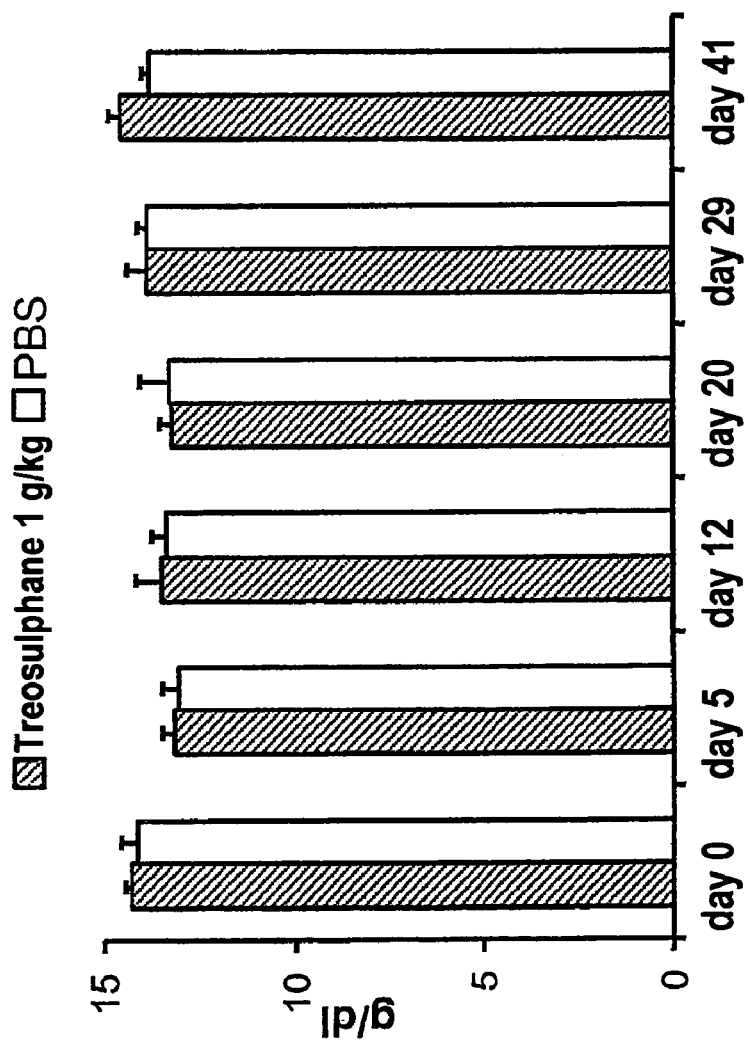
FIG. 6: Haemoglobin (Hb) in MOG-EAE treatment with treosulfan on day 0.
Figure 7:
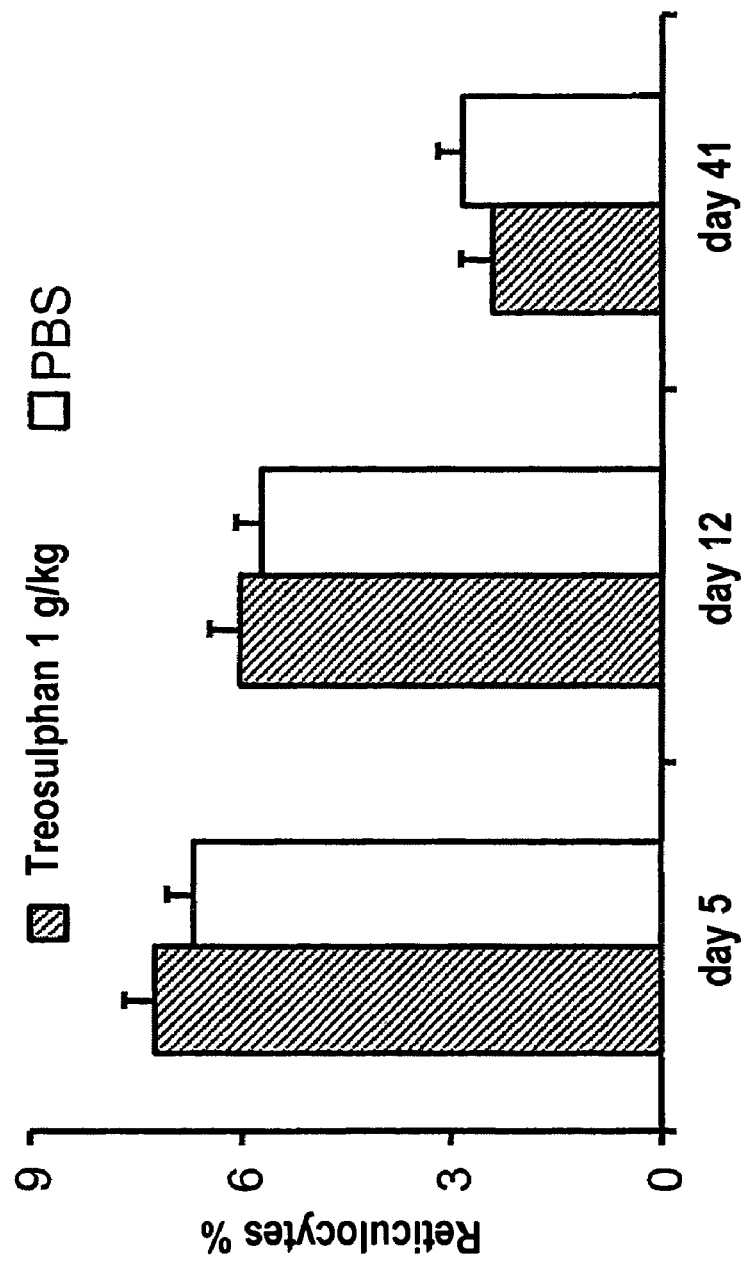
FIG. 7: Reticulocytes in MOG-EAE treatment with treosulfan on day 0.
Figure 8:
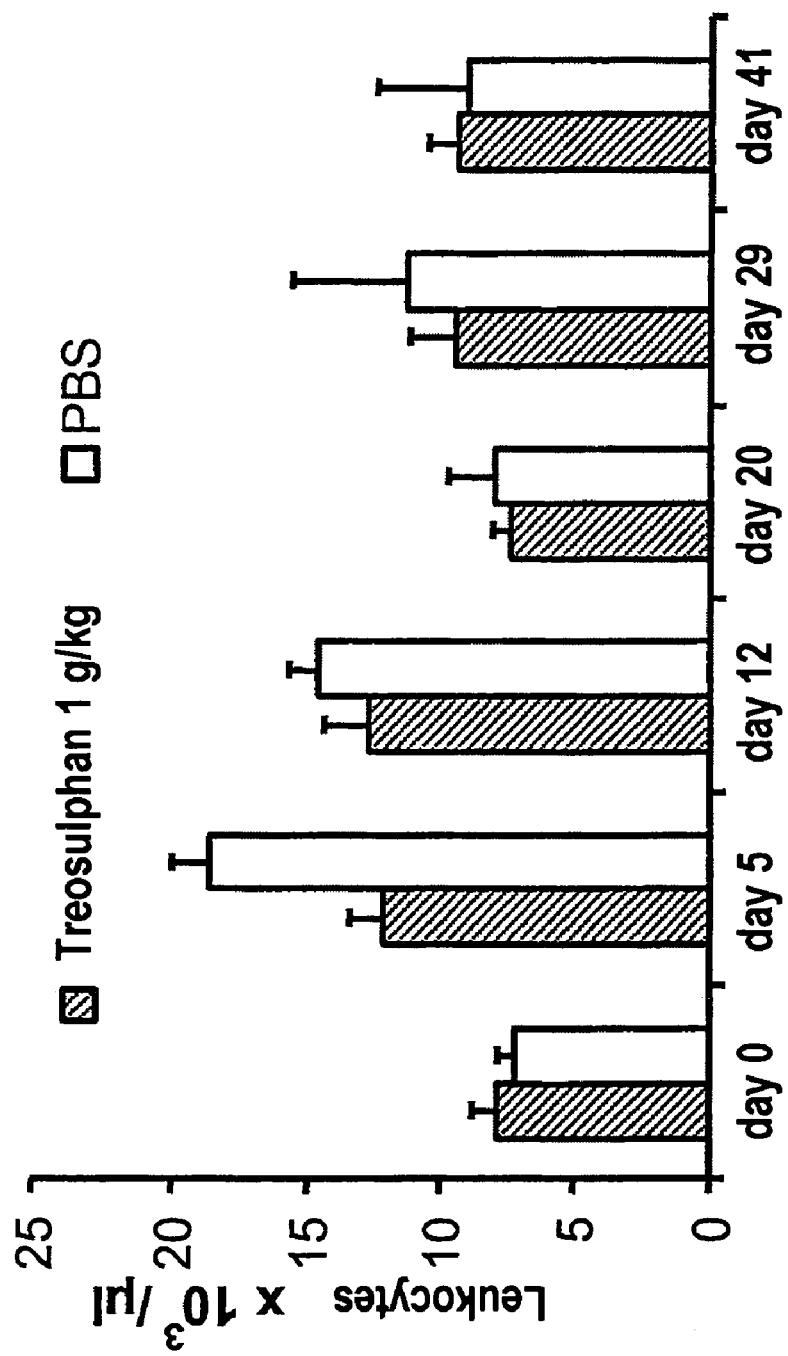
FIG. 8: Leukocytes in MOG-EAE treatment with treosulfan on day 0.
Figure 9:
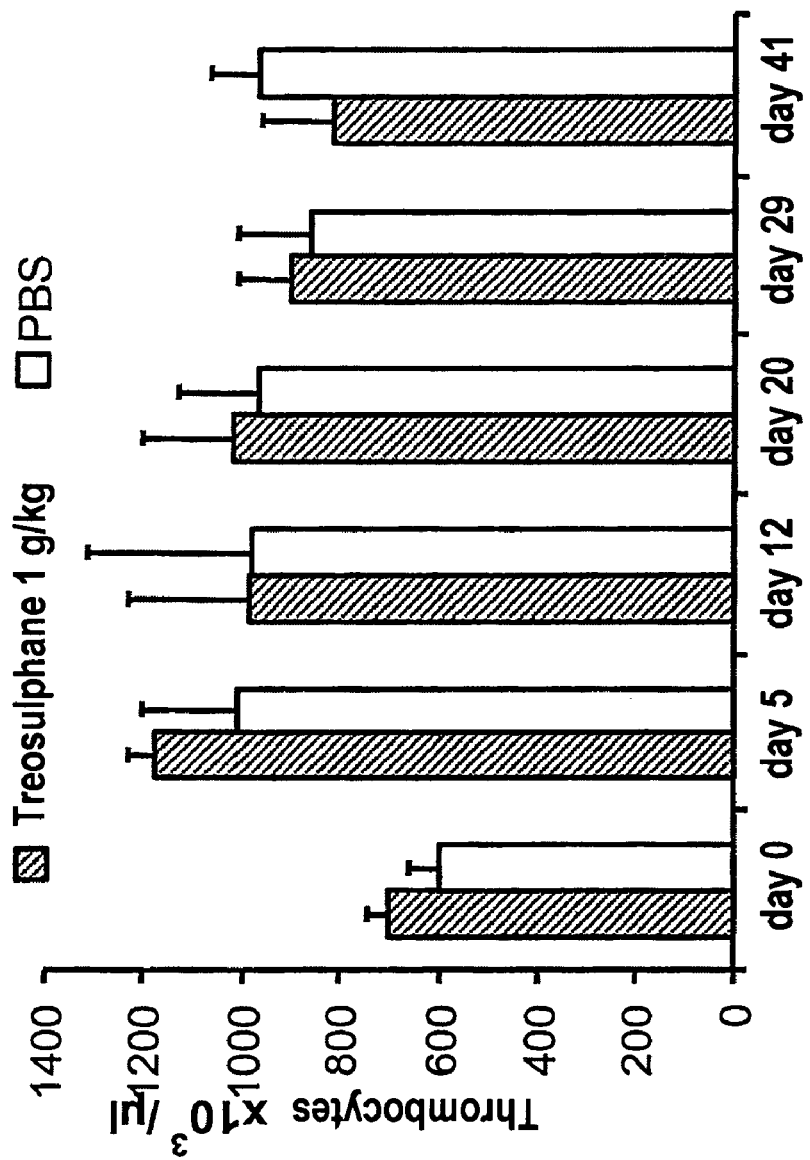
FIG. 9: Thrombocytes in MOG-EAE treatment with treosulfan on day 0.
Figure 10:
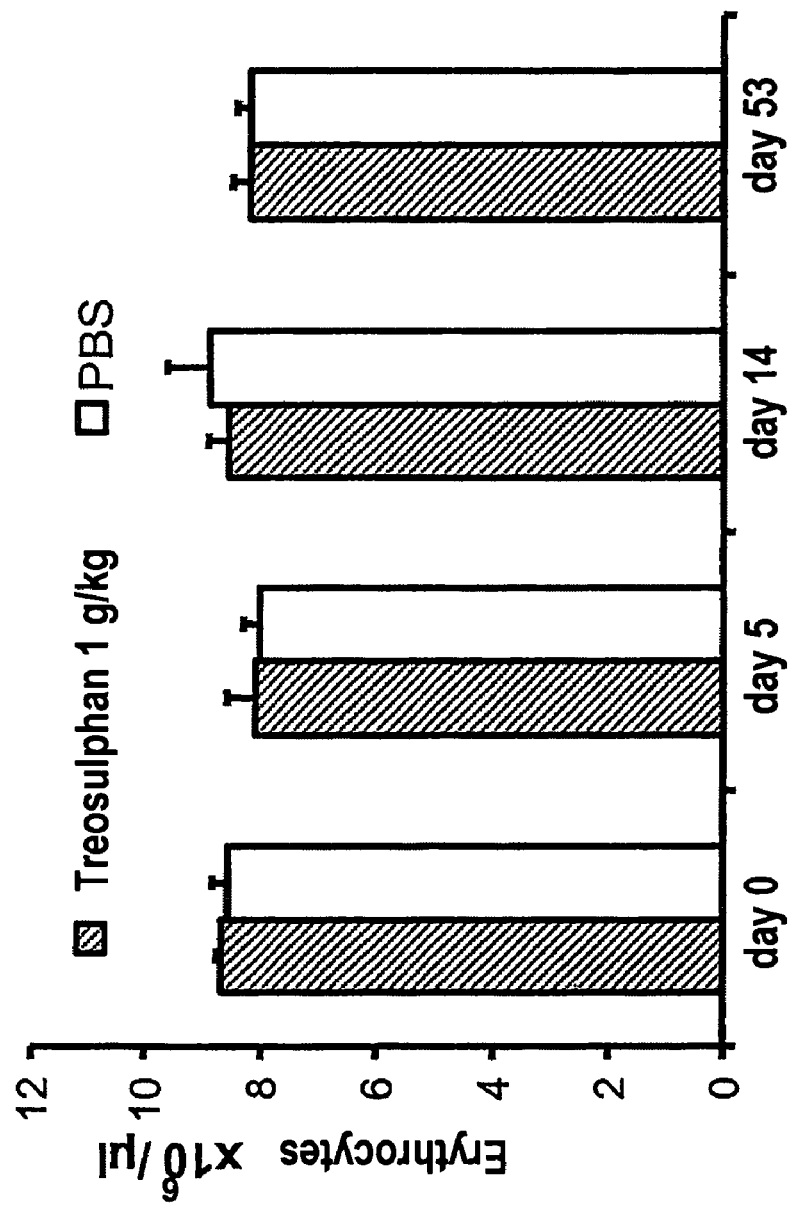
FIG. 10: Erythrocytes in MOG-EAE treatment with treosulfan on day 14 p.i.
Figure 11:
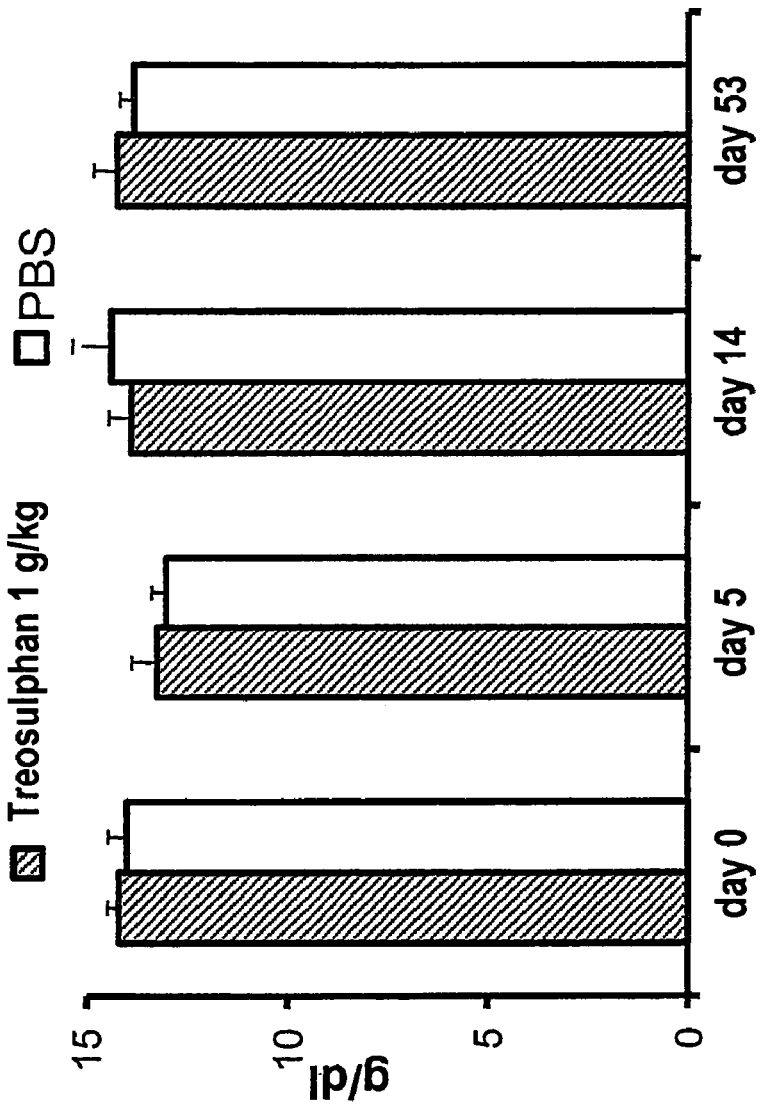
FIG. 11: Haemoglobin (Hb) in MOG-EAE treatment with treosulfan on day 14 p.i.
Figure 12:
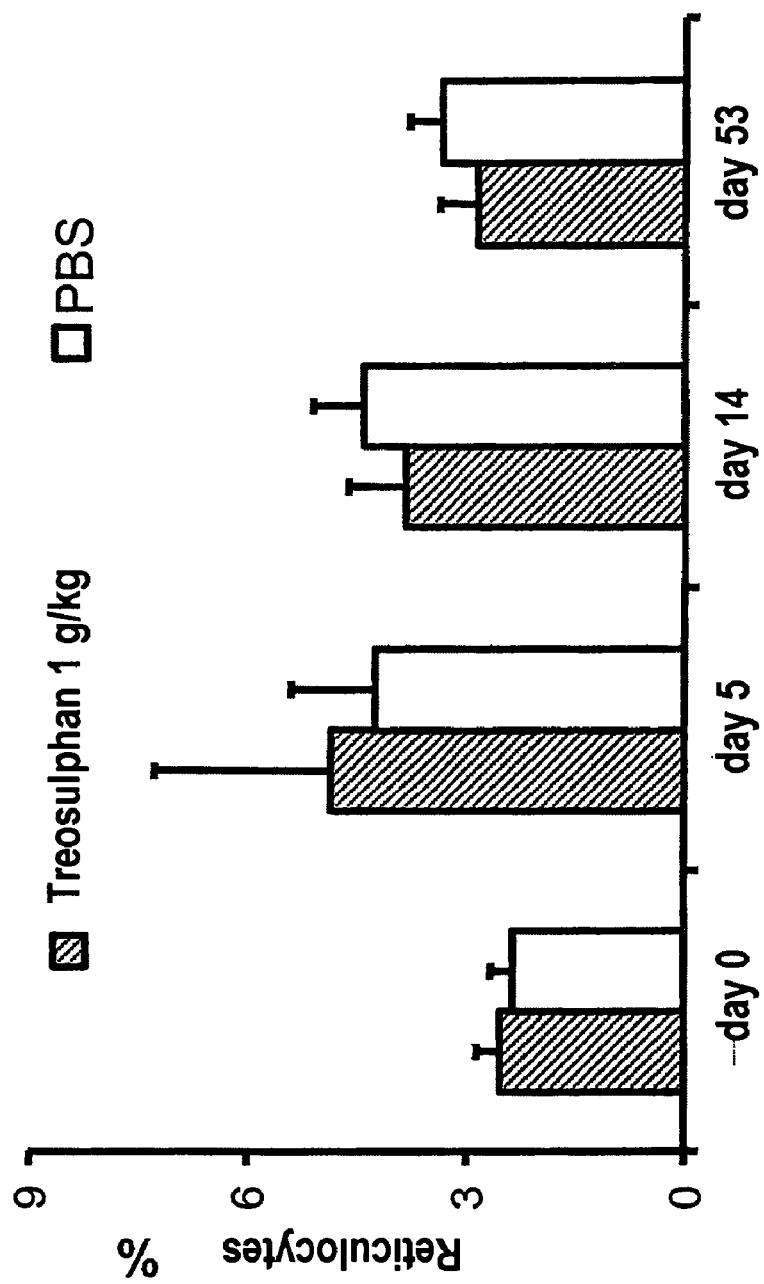
FIG. 12: Reticulocytges in MOG-EAE treatment with treosulfan on day 14 p.i.
Figure 13:
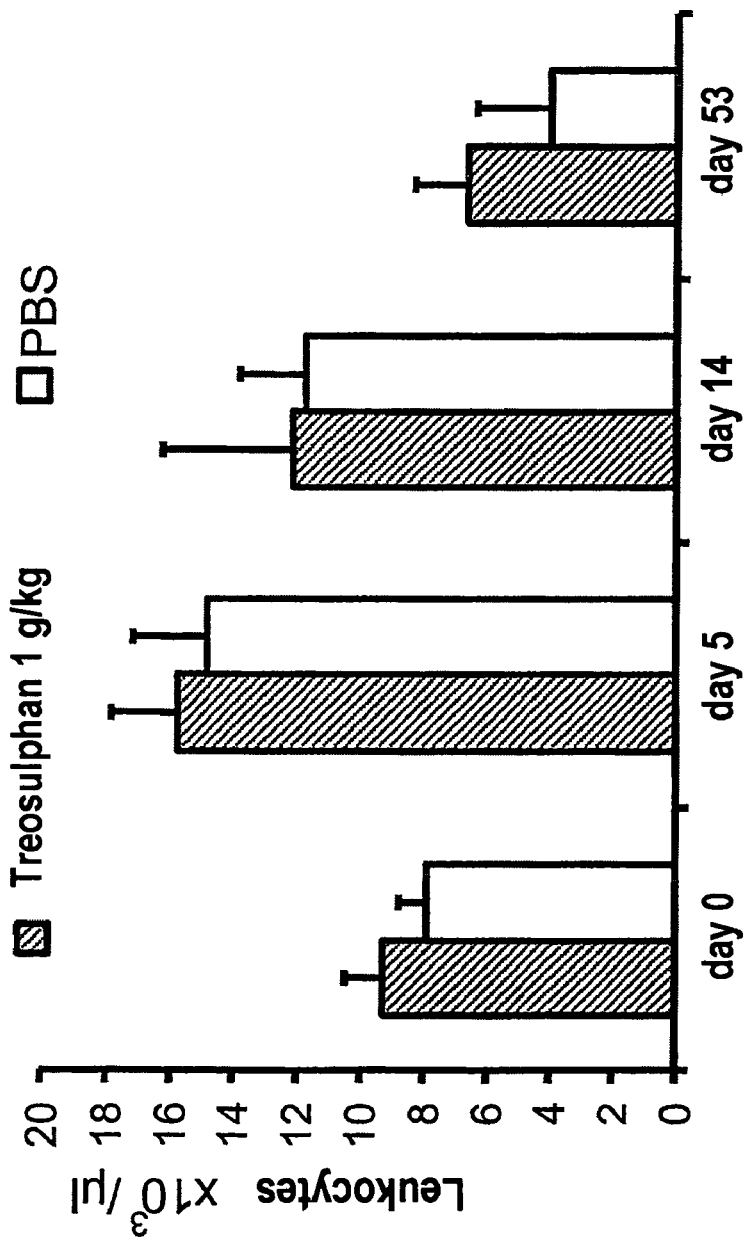
FIG. 13: Leukocytes in MOG-EAE treatment with treosulfan on day 14 p.i.
Figure 14:
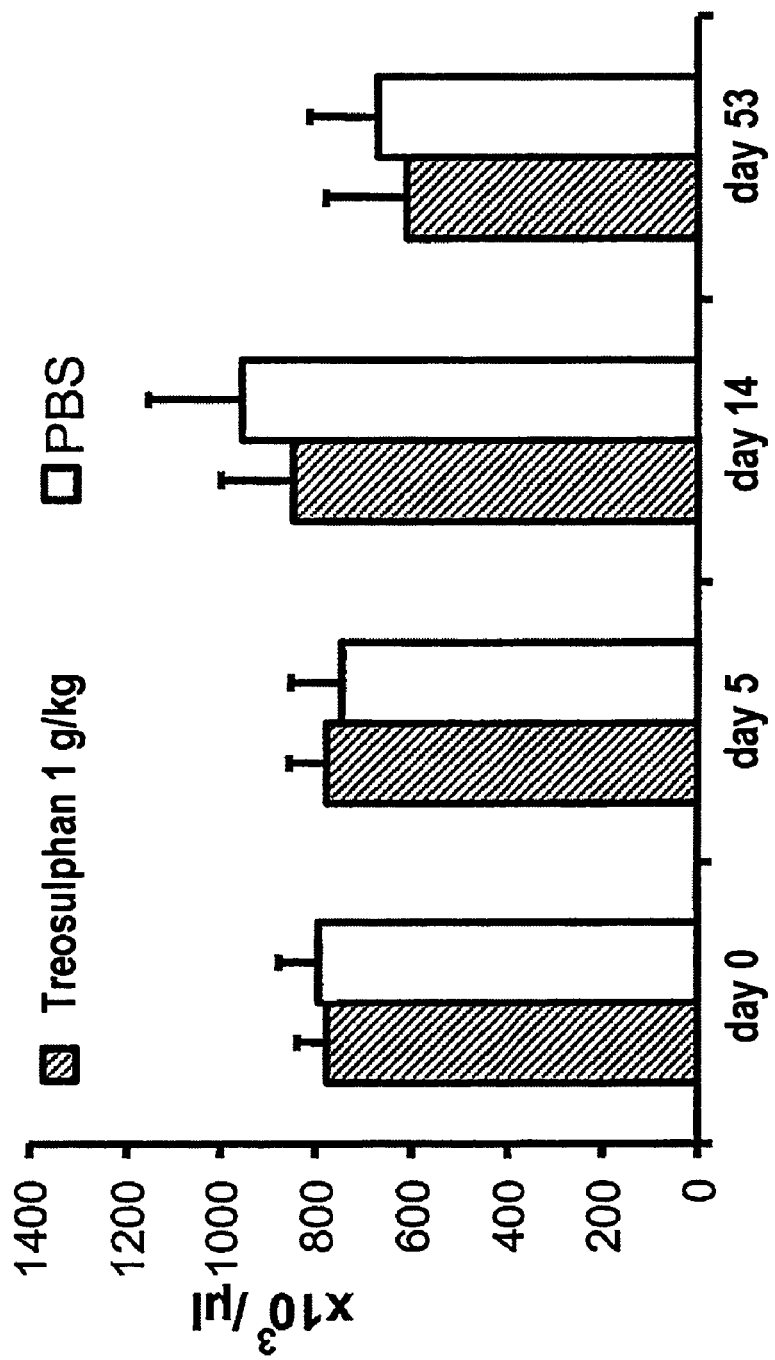
FIG. 14: Thrombocytes in MOG-EAE treatment with treosulfan on day 14 p.i.
Figure 15:
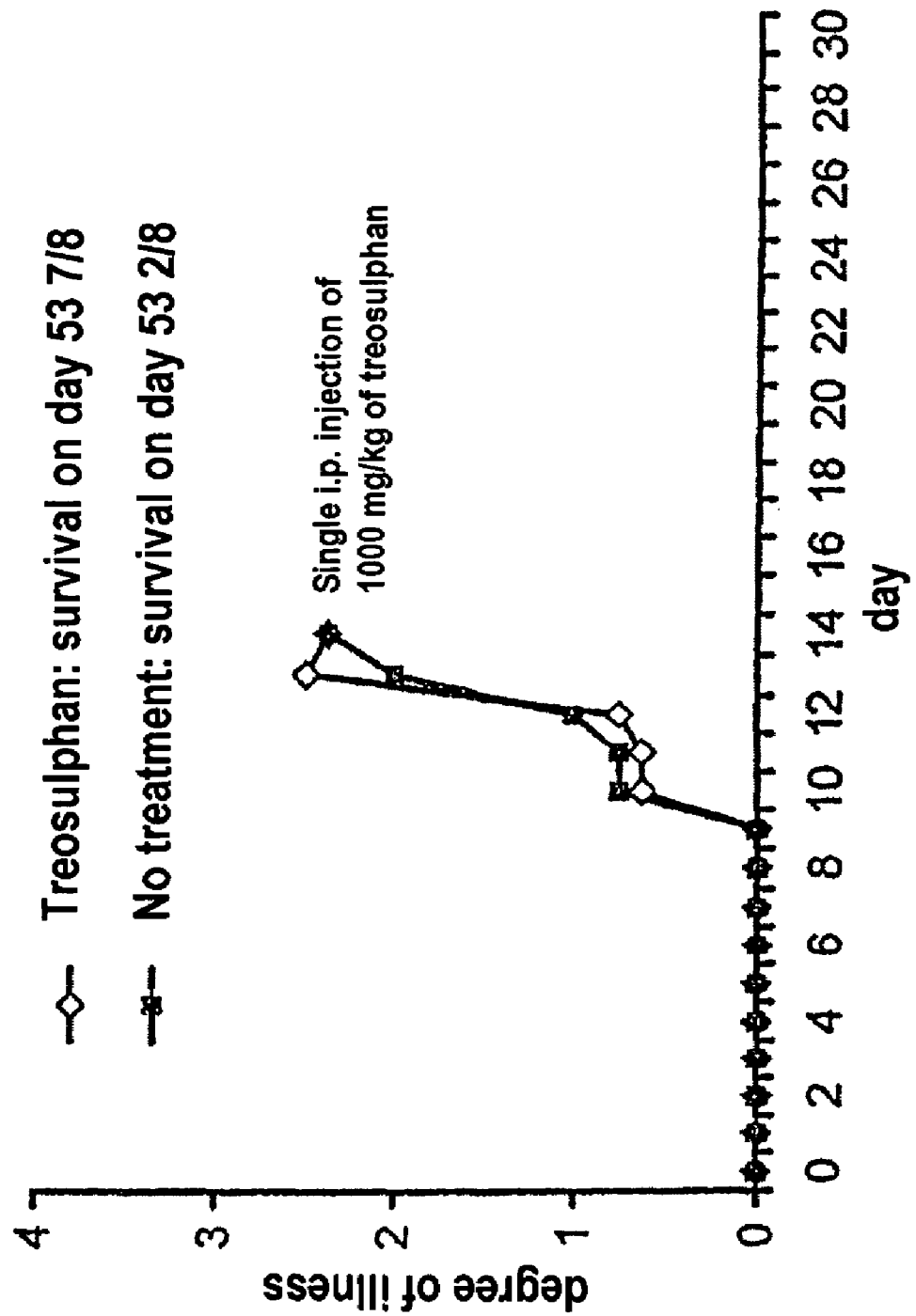
FIG. 15: Single i.p. injection of 1,000 mg/kg treosulfan.
Figure 16:
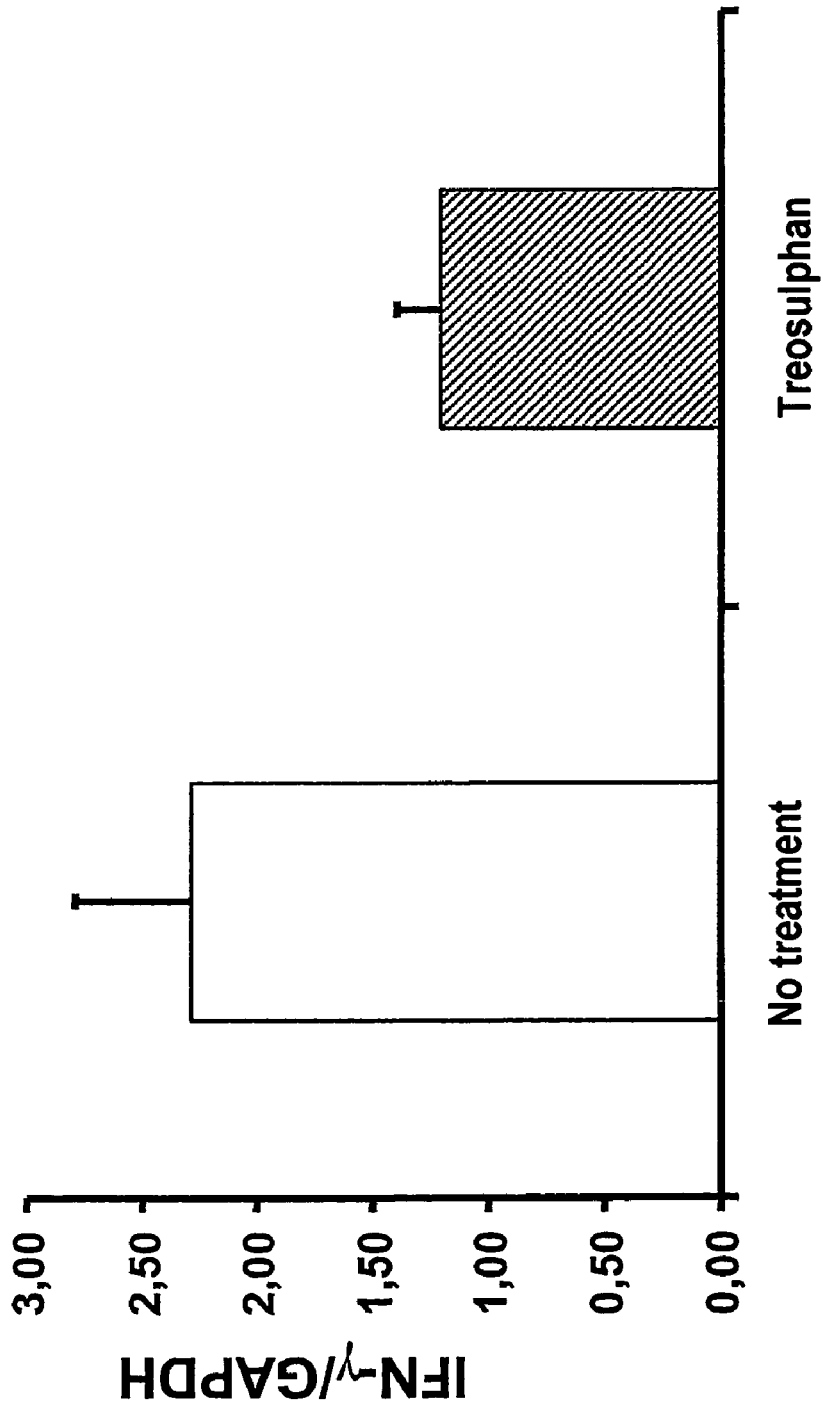
FIG. 16: Quantitative PCR for IFN-treatment with treosulfan on day 0.
Figure 17:
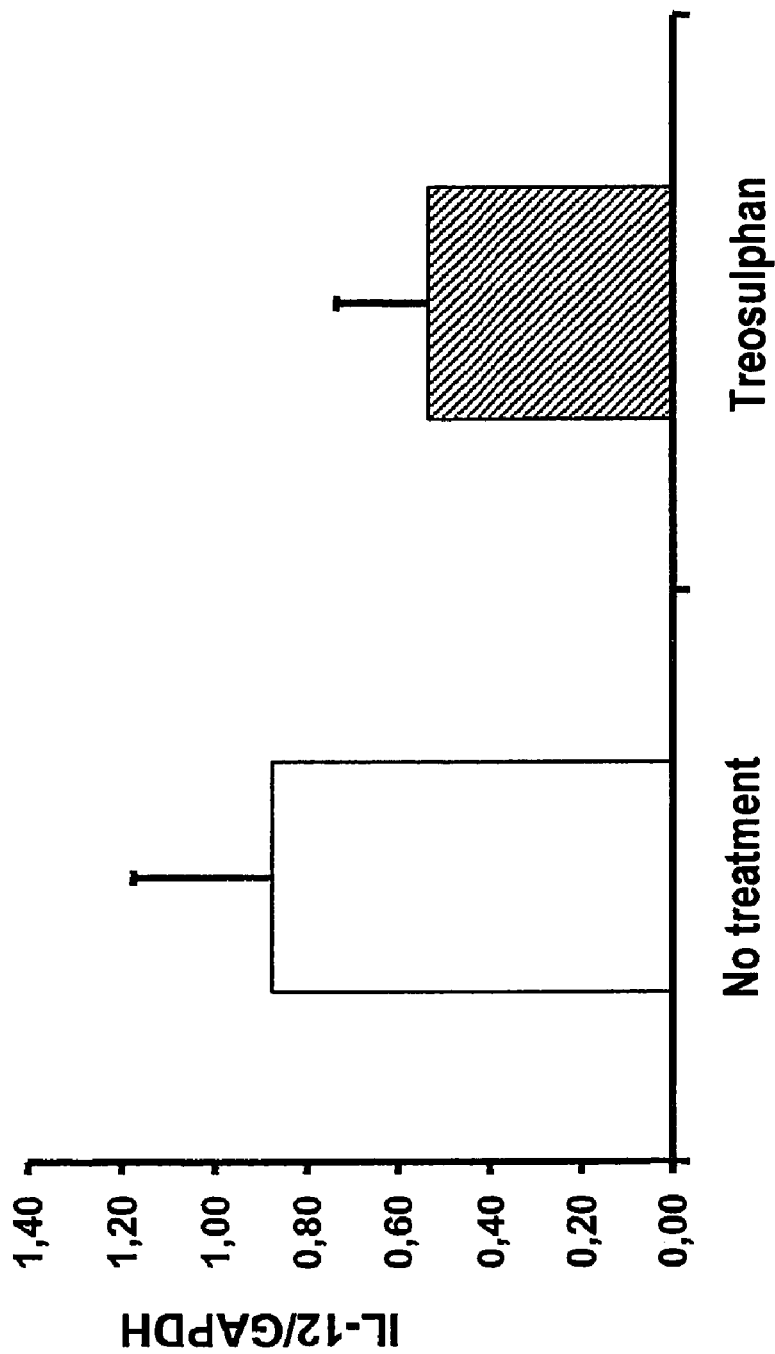
FIG. 17: Quantitative PCR for IL-12 treatment with treosulfan on day 0.

The invention claimed is:

1. A method of treating multiple sclerosis (MS) comprising administering at least one compound selected from the group consisting of treosulfan, busulfan, dimethyl busulfan, pentasulfan and hepsulfam to a person in need of such treatment, said method not comprising stem cell transplantation.

2. A method of treating multiple sclerosis (MS) comprising administering at least one compound selected from the group of treosulfan, busulfan, dimethyl busulfan, pentasulfan and hepsulfam to a person in need of such treatment, wherein administration of said at least one compound leads to an improvement of the ambulation index of said person, said method not comprising stem cell transplantation.

3. The method of claim 1, wherein said MS is a relapsing-remitting, primary progressive or secondary progressive MS.

4. The method of claim 2, wherein said MS is a relapsing-remitting, primary progressive or secondary progressive MS.

5. A method of treating multiple sclerosis (MS) comprising administering at least one compound of formula (I) to a person in need of such treatment, said method not comprising stem cell transplantation, wherein

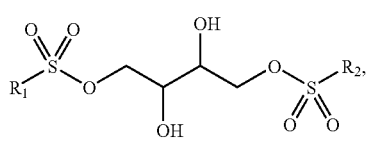

(I)

wherein $R_1$ and $R_2$ are the same or different and are a linear $C_{1-7}$ alkyl or a $C_{3-7}$ branched alkyl.

6. A method of treating multiple sclerosis (MS) comprising administering at least one compound of formula (I) to a person in need of such treatment, wherein administration of said at least one compound leads to an improvement of the ambulation index of said person, said method not comprising stem cell transplantation, wherein

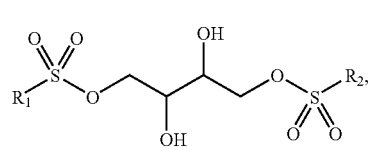

(I)

wherein $R_1$ and $R_2$ are the same or different and are a linear $C_{1-7}$ alkyl or a $C_{3-7}$ branched alkyl.

7. The method of claim 1, wherein said at least one compound selected from the group consisting of treosulfan, busulfan, dimethyl busulfan, pentasulfan and hepsulfam is administered in the amount of 1 to 10 grams per $m^2$ of body surface.

8. The method of claim 2, wherein said at least one compound selected from the group consisting of treosulfan, busulfan, dimethyl busulfan, pentasulfan and hepsulfam is administered in the amount of 1 to 10 grams per $m^2$ of body surface.

9. The method of claim 7, wherein said at least one compound selected from the group consisting of treosulfan, busulfan, dimethyl busulfan, pentasulfan and hepsulfam is administered in the amount of 3 to 9 grams per $m^2$ of body surface.

10. The method of claim 8, wherein said at least one compound selected from the group consisting of treosulfan, busulfan, dimethyl busulfan, pentasulfan and hepsulfam is administered in the amount of 3 to 9 grams per $m^2$ of body surface.

11. The method of claim 7, wherein said at least one compound selected from the group consisting of treosulfan, busulfan, dimethyl busulfan, pentasulfan and hepsulfam is administered in the amount of 5 to 8 grams per $m^2$ of body surface.

12. The method of claim 8, wherein said at least one compounds selected from the group consisting of treosulfan, busulfan, dimethyl sulfan, pentasulfan and hepsulfam is administered in the amount of 5 to 8 per $m^2$ of body surface.

13. The method of claim 1, wherein said method further comprises administration of at least one of interferon-β and glatriamer acetate.

14. The method of claim 2, wherein said method further comprises administration of at least one interferon-β and glatriamer acetate.

15. The method of claim 5, wherein said method further comprises administration of at least one of interferon-β and glatriamer acetate.

16. The method of claim 6, wherein said method further comprises administration of at least one of interferon-β and glatriamer acetate.

17. The method according to claim 1, wherein said administering comprises administration of infusion solution or an oral formulation.

18. The method according to claim 2, wherein said administering comprises administration of infusion solution or an oral formulation.

19. The method of claim 5, wherein said MS is a relapsing-remitting, primary progressive or secondary progressive MS.

20. The method of claim 6, wherein said MS is a relapsing-remitting, primary progressive or secondary progressive MS.

21. The method of claim 5, wherein said at least one compound is administered in the amount of 1 to 10 grams per $m^2$ of body surface.

22. The method of claim 6, wherein said at least one compound is administered in the amount of 1 to 10 grams per $m^2$ of body surface.

23. The method of claim 22, wherein said at least one compound is administered in the amount of 3 to 9 grams per $m^2$ of body surface.

24. The method of claim 22, wherein said at least one compound is administered in the amount of 3 to 9 grams per $m^2$ of body surface.

25. The method of claim 21, wherein said at least one compound is administered in the amount of 5 to 8 grams per $m^2$ of body surface.

26. The method of claim 22, wherein said at least one compound is administered in the amount of 5 to 8 grams per $m^2$ of body surface.

27. The method of claim 5, wherein said method further comprises administration of at least one of interferon-β and glatriamer acetate.

28. The method of claim 6, wherein said method further comprises administration of at least one of interferon-β and glatriamer acetate.

29. The method according to claim 5, wherein said administering comprises administration of infusion solution or an oral formulation.

30. The method according to claim 6, wherein said administering comprises administration of infusion solution or an oral formulation.

* * * * *